(12) United States Patent
Van Der Heide et al.

(10) Patent No.: US 10,093,602 B2
(45) Date of Patent: Oct. 9, 2018

(54) PROCESS FOR THE CONVERSION OF SACCHARIDE-CONTAINING FEEDSTOCK

(71) Applicant: SHELL OIL COMPANY, Houston, TX (US)

(72) Inventors: Evert Van Der Heide, Amsterdam (NL); Pieter Huizenga, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/519,843

(22) PCT Filed: Sep. 9, 2015

(86) PCT No.: PCT/EP2015/070566
§ 371 (c)(1),
(2) Date: Apr. 18, 2017

(87) PCT Pub. No.: WO2016/038071
PCT Pub. Date: Mar. 17, 2016

(65) Prior Publication Data
US 2017/0240491 A1    Aug. 24, 2017

(30) Foreign Application Priority Data
Sep. 9, 2014    (EP) .................................. 14184115

(51) Int. Cl.
*C07C 29/132*    (2006.01)

(52) U.S. Cl.
CPC ................................ *C07C 29/132* (2013.01)

(58) Field of Classification Search
CPC ................................................. C07C 29/132
See application file for complete search history.

(56) References Cited

U.S. PATENT DOCUMENTS

| | | | |
|---|---|---|---|
| 2011/0312488 A1* | 12/2011 | Chen | B01J 21/18 502/74 |
| 2011/0313212 A1 | 12/2011 | Kalnes et al. | |
| 2012/0315677 A1* | 12/2012 | Genta | C12P 19/14 435/105 |

OTHER PUBLICATIONS

Liu et al., Angewandte Chemie International Edition, vol. 51, Issue 13, Mar. 26, 2012, p. 3249.
International Search Report and Written Opinion received for PCT Patent Application No. PCT/EP2015/070566, dated Oct. 30, 2015, 7 pages.

* cited by examiner

*Primary Examiner* — Pancham Bakshi
*Assistant Examiner* — Mark R Luderer

(57) ABSTRACT

The invention provides a process for the catalytic conversion of a saccharide-containing feedstock in a reactor, wherein saccharide-containing feedstock is provided to the reactor as a feed stream through a feed pipe and is contacted with a catalyst system in the reactor and wherein, as the saccharide-containing feedstock is fed through the feed pipe, a solvent stream, initially comprising essentially no saccharide, is fed along the internal walls of the feed pipe.

11 Claims, 2 Drawing Sheets

PROCESS FOR THE CONVERSION OF SACCHARIDE-CONTAINING FEEDSTOCK

PRIORITY CLAIM

The present application is the National Stage (§ 371) of International Application No. PCT/EP2015/070566, filed Sep. 9, 2015, which claims priority from 14184115.5, filed Sep. 9, 2014 incorporated herein by reference.

FIELD OF THE INVENTION

The present invention relates to a process for the catalytic conversion of a saccharide-containing feedstock.

BACKGROUND OF THE INVENTION

In recent years increasing efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. An example of such a process is described in Angew. Chemie. Int. Ed. 2012, 51, 3249 and WO 2011/0313212 and may be used to provide ethylene glycol and 1,2-propylene glycol, which are valuable materials with a multitude of commercial applications, e.g. as heat transfer media, antifreeze, and precursors to polymers, such as PET. Ethylene and 1,2-propylene glycols are traditionally made on an industrial scale by hydrolysis of the corresponding alkylene oxides, which are the oxidation products of ethylene and propylene, produced from fossil fuels.

A major problem encountered in the catalytic conversion of saccharides by known methods is the degradation of the saccharides in reactor feed pipes at high temperatures. Such degradation can lead to fouling and blocking of the pipes. One way to limit this problem is to supply the feed in the pipes at a lower temperature than the degradation temperature of the saccharides. The feed is, therefore, also at a lower temperature than the material in the reactor. However, degradation, fouling and blocking will still occur at the point where the feed pipes enter the reactor, due to the inevitable increase in temperature at this point.

Fouling and blocking of the feed pipes lead to reactor shut-downs for cleaning and/or replacement of the feed pipes and connections. This translates to higher running costs and reduced productivity. It would, therefore, be highly desirable to provide a method to reduce saccharide degradation and the related fouling and blocking in reactor feed pipes.

SUMMARY OF THE INVENTION

Accordingly, the present invention provides a process for the catalytic conversion of a saccharide-containing feedstock in a reactor, wherein saccharide-containing feedstock is provided to the reactor as a feed stream through a feed pipe and is contacted with a catalyst system in the reactor and wherein, as the saccharide-containing feedstock is fed through the feed pipe, a solvent stream, initially comprising essentially no saccharide, is fed along the internal walls of the feed pipe.

DETAILED DESCRIPTION OF THE INVENTION

Figure 1:
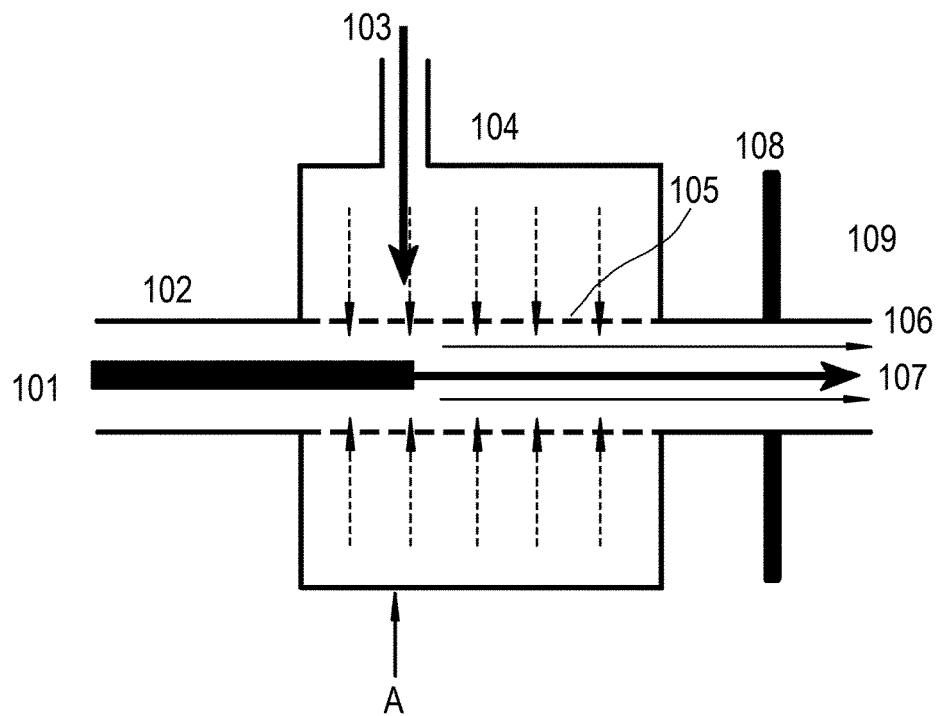
FIGS. 1 to 4 are schematic diagrams showing aspects of exemplary, but non-limiting, embodiments of the process described herein.

The present inventors have surprisingly found that saccharide degradation in feed pipes and at the point of entry to a reactor can be significantly decreased by preventing contact of the saccharide-containing feedstock with the internal walls of the feed pipe by passing a solvent stream along the internal walls of the feed pipe.

The process requires a saccharide-containing feedstock. Said feedstock suitably comprises at least 1 wt % saccharide in a solvent. Preferably the saccharide-containing feedstock comprises at least 2 wt %, more preferably at least 5 wt %, even more preferably at least 10 wt %, most preferably at least 20 wt % saccharide in a solvent. Suitably, the saccharide-containing feedstock contains no more than 50 wt %, preferably no more than 40 wt % saccharide in a solvent.

As well as the solvent stream, one or more further feed streams comprising solvent may also be added to the reactor together with the saccharide-containing feedstock, either through the same feed pipe or at a separate point in the reactor.

It is envisaged that the composition and amount of the saccharide-containing feedstock, the solvent stream, the contents of the reactor and the amount of any further feed stream added to the reactor will be coordinated such that the concentration of saccharide in the solvent in the reactor while the reaction is proceeding is at least 0.01 wt % saccharide in solvent. Preferably, the concentration of saccharide in solvent in the reactor is at least 0.02 wt %. Most preferably, the concentration of saccharide in solvent in the reactor is at least 0.25 wt %. It is envisaged that the composition and amount of the saccharide-containing feedstock, the solvent stream, the contents of the reactor and the amount of any further feed stream added to the reactor will be coordinated such that the concentration of saccharide in the solvent in the reactor while the reaction is proceeding is at most 5 wt % saccharide in solvent. Preferably, the concentration of saccharide in solvent in the reactor is at most 2 wt %. Most preferably, the concentration of saccharide in solvent in the reactor is at most 1.5 wt %

The saccharide-containing feedstock comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof. If the saccharide-containing feedstock comprises oligosaccharides or polysaccharides, it is preferable that it is subjected to pre-treatment before being fed to the reactor in a form that can be converted to glycols when contacted with hydrogen in the reactor in the presence of a suitable catalyst system. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the saccharide-containing feedstock that is fed to the reactor, after pre-treatment if necessary, comprises one or more saccharide selected from the group consisting of glucose, sucrose and starch. Said saccharide is suitably present as a solution, a suspension or a slurry in the solvent.

The solvent stream comprises solvent and, initially essentially no saccharide. It is envisaged that a small amount of saccharide may become dissolved or suspended in the solvent stream as it passes through the feed pipe. The solvent in the solvent stream may be the same as or different to the solvent in the saccharide-containing feedstock. Suitably, the solvent in the solvent stream is water, a $C_1$ to $C_6$ alcohol, or mixtures thereof. Preferably, the solvent is water.

The solvent in the saccharide-containing feedstock may be water, a $C_1$ to $C_6$ alcohol, or mixtures thereof. Preferably, the solvent is water.

As well as the solvent provided in the saccharide-containing feedstock and the solvent stream there may also be further solvent already present in the reactor and/or added to the saccharide-containing feedstock as set out above. Said solvent is also suitably water, a $C_1$ to $C_6$ alcohol, or mixtures thereof. Preferably, all solvents are the same. More preferably, all solvents comprise water. Most preferably, all solvents are water.

Any reactor type suitable for a semi-batch or continuous process, requiring a saccharide starting material to be added as a feed stream through a feed pipe, may be used in the process of the invention. Preferably, the process of the invention is carried out as a continuous flow process, wherein a reaction product is continuously removed from the reactor.

In this embodiment, any reactor type suitable for a continuous flow process in which reaction product is continuously removed from the reactor may be used for the process of the present invention. For example, suitable reactor systems include ebullated catalyst bed reactor systems, immobilized catalyst reactor systems having catalyst channels, augured reactor systems, fluidized bed reactor systems, mechanically mixed reactor systems and slurry reactor systems, also known as a three phase bubble column reactor systems, and combinations thereof.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the temperature in the reactor is above the degradation temperature of the one or more saccharides in the saccharide feedstock. Preferably, the reactor is heated to a temperature within these limits before addition of any starting material and is maintained at such a temperature until all reaction is complete.

To reduce degradation of the saccharide-containing feedstock, the temperature of the saccharide-containing feedstock in the feed pipe is suitably, at least initially, maintained below the degradation temperature of the saccharide contained therein. As used herein, the term degradation temperature relates to the temperature at which 1% of the saccharide present is degraded within an hour and will vary depending on the saccharides present.

However, in one embodiment of the present invention the temperature of the saccharide-containing feedstock in the feed pipe may advantageously be maintained above the degradation temperature of the saccharides contained therein as, in the process of the present invention, the saccharide-containing feedstock will not come into contact with the walls of the feed pipe. As used herein, the term degradation temperature relates to the temperature at which 1% of the saccharide present is degraded within an hour and will vary depending on the saccharides present.

Preferably, in order to maintain the temperature within the reactor, the temperature of the saccharide-containing feedstock is within 10° C. of the temperature of the reactor.

The temperature of the solvent stream may suitably be anywhere in the range of from ambient temperature to less than the boiling point of the solvent stream under the conditions of the process. In order to maintain the temperature within the reactor, it is preferred that the temperature of the solvent stream is within the range of from 10° C. below to 100° C. above the temperature of the reactor.

In one preferred embodiment of the invention, the saccharide-containing feedstock is initially below the degradation temperature of the saccharide and the temperature of the solvent stream is above the degradation temperature of the saccharide with the result that, as the saccharide-containing feedstock and the solvent stream are mixed as they enter the reactor, their combined temperature is within 2° C., preferably 1° C. of the temperature of the reactor. As used herein, the term degradation temperature relates to the temperature at which 1% of the saccharide present is degraded within an hour and will vary depending on the saccharides present.

Any suitable method may be used for creating a coaxial flow of the solvent stream and the saccharide-containing feedstock stream, such that the two streams are flowing in the same direction, with the solvent stream passing along the walls of the feed pipe and the saccharide-containing feedstock passing through the centre of the feed pipe with little or no contact between the saccharide-containing feedstock and the walls of the feed pipe.

Methods to achieve this include providing the solvent stream to the internal walls of the feed pipe through a permeable section of said feed pipe or providing the solvent stream and the saccharide-containing feedstock to the feed pipe through concentric pipes in order to provide a concentric flow.

The pressure in the reactor is suitably at least 1 MPa, preferably at least 2 MPa, more preferably at least 3 MPa. The pressure in the reactor is suitably at most 16 MPa, preferably at most 12 MPa, more preferably at most 10 MPa, even more preferably at most 8 MPa, most preferably at most 6 MPa. Preferably, the reactor is pressurised to a pressure within these limits by addition of hydrogen before addition of any saccharide-containing feedstock. The pressure of hydrogen is maintained by addition of hydrogen as a separate feed stream throughout the process.

Preferably, the process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents, before the reaction starts.

In one embodiment of the invention, the catalytic conversion of a saccharide-containing feedstock in a reactor comprises the conversion of one or more saccharides in the presence of hydrogen and a catalyst system to ethylene glycol and 1,2-propylene glycol. In this embodiment of the invention, the catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

Under continuous flow operation, an effluent stream comprising ethylene glycol and 1,2-propylene glycol is continuously removed from the reactor. Said effluent stream may also contain water, hydrogen, unreacted saccharide, intermediates, by-products and catalyst materials. Said catalyst materials may be the result of decomposition of the catalyst system in the reactor or may be catalyst material present as part of an at least partially homogeneous catalyst system. Such catalyst materials will need to be separated from the effluent stream and optionally recycled to the reactor or a reactor feed stream.

The remaining effluent stream will then require separation and purification of the desired products. Unreacted saccharides and intermediates may be separated and recycled to the saccharide-containing feedstock. Hydrogen and water may also be separated and recycled to reactor feed streams.

Embodiments of the present invention will now be described by way of example only and with reference to the accompanying non-limiting figures.

In FIG. 1, a saccharide-containing feedstock stream 101 passes along a feed pipe 102. A solvent stream 103 is fed into a vessel 104 which surrounds the feed pipe 102. Within this vessel, the wall 105 between the vessel and the feed pipe is comprises a solvent permeable material through which the solvent passes, creating a co-axial flow of solvent 106 around a central flow 107 of saccharide-containing feedstock as the streams enter the reactor 109, through the reactor wall 108.

Figure 2:
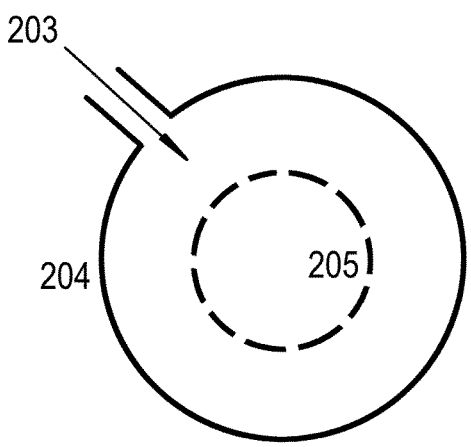

FIG. 2 shows a cross section across the system shown in FIG. 1 at point A. At this point the wall of the feed pipe 205 comprises a permeable material. The feed pipe is surrounded by a vessel 204 which is supplied with solvent 203. The solvent can pass through the permeable material to provide a co-axial flow along the internal walls of the feed pipe as shown in FIG. 1.

Figure 3:
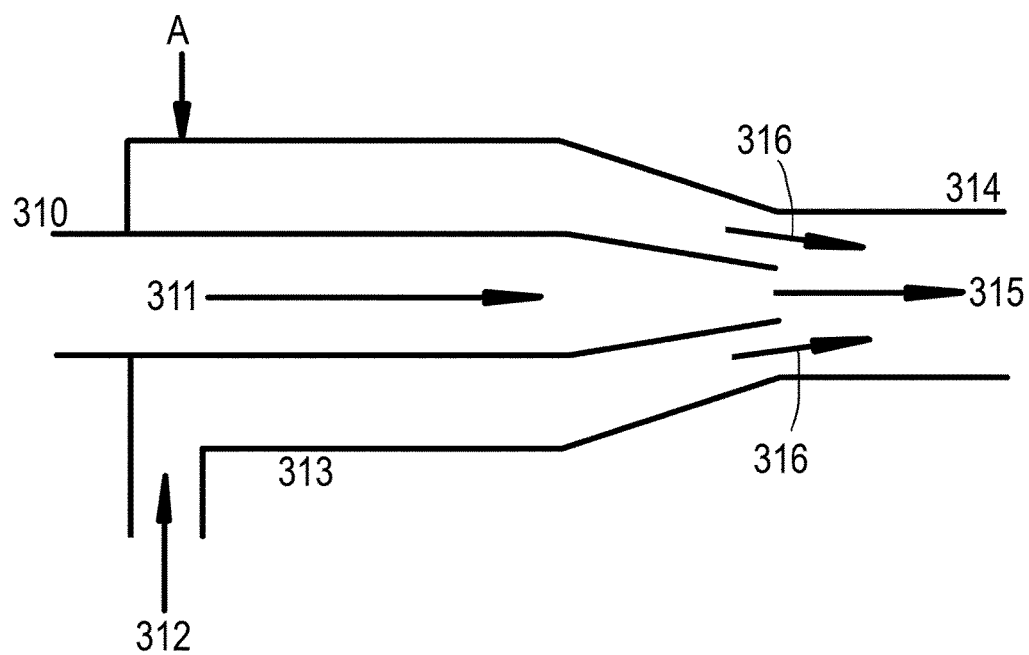

FIG. 3 shows a different embodiment of the process of the invention. In this embodiment, a saccharide-containing feedstock stream 311 passes along a pipe 310. A solvent stream 312 is fed into an outer pipe 313 which surrounds the pipe 310. The two streams are combined, creating a co-axial flow of solvent 316 around a central flow 315 of saccharide-containing feedstock as the streams enter the feed pipe 314 supplying the reactor.

Figure 4:
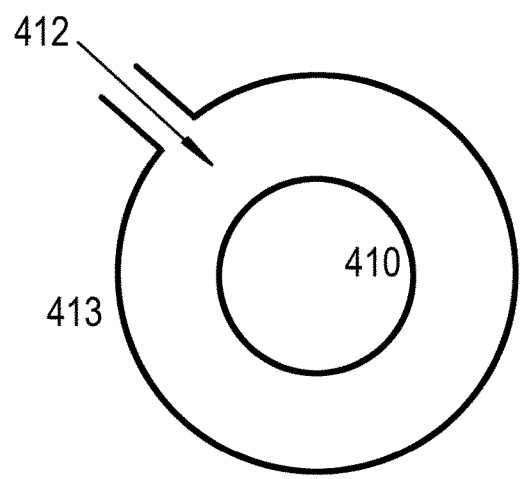

FIG. 4 shows a cross section across the system shown in FIG. 3 at point A. At this point the wall of the pipe 310 is surrounded by a vessel 413 which is supplied with solvent 412.

That which is claimed is:

1. A process for the catalytic conversion of a saccharide-containing feedstock in a reactor to a glycol, wherein saccharide-containing feedstock is provided to the reactor as a feed stream through a feed pipe having a first section and a second section and is contacted with a catalyst system in the reactor and wherein, as the saccharide-containing feedstock is fed through the second section of the feed pipe, a solvent stream, initially comprising essentially no saccharide, is fed along the internal walls of the second section of the feed pipe to provide a co-axial flow of the solvent stream around the saccharide-containing feedstock.

2. A process according to claim 1, wherein the solvent stream is provided to the internal walls of the second section of the feed pipe through a permeable section of the first section of the feed pipe.

3. A process according to claim 1, wherein the solvent stream and the saccharide-containing feedstock are provided to the second section of the feed pipe through concentric pipes in order to provide the co-axial flow.

4. A process according to claim 1, wherein the temperature of the saccharide-containing feedstock is initially below the degradation temperature of the saccharide and the temperature of the solvent stream is initially higher than the degradation temperature of the saccharide.

5. A process according to claim 1, wherein the saccharide containing feedstock is also contacted with hydrogen in the reactor.

6. A process according to claim 1, wherein the catalytic conversion of a saccharide-containing feedstock comprises the conversion of said feedstock into ethylene glycol and 1,2-propylene glycol in the presence of a catalyst system.

7. A process according to claim 6, wherein the catalyst system comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

8. A process according to claim 1, wherein the solvent comprises water.

9. A process according to claim 1, wherein the saccharide-containing feedstock comprises one or more of glucose, sucrose and starch.

10. A process according to claim 1, wherein the temperature in the reactor is in the range of from 150 to 250° C. and the pressure in the reactor is in the range of from 1 to 16 MPa.

11. A process for the catalytic conversion of a saccharide-containing feedstock in a reactor, wherein saccharide-containing feedstock is provided to the reactor as a feed stream through a feed pipe and is contacted with a catalyst system in the reactor and wherein, as the saccharide-containing feedstock is fed through the feed pipe, a solvent stream, initially comprising essentially no saccharide, is fed along the internal walls of the feed pipe, wherein the temperature of the saccharide-containing feedstock is initially below the degradation temperature of the saccharide and the temperature of the solvent stream is initially higher than the degradation temperature of the saccharide.

* * * * *